(12) United States Patent
Johnson et al.

(10) Patent No.: US 10,813,694 B2
(45) Date of Patent: Oct. 27, 2020

(54) LIGHT BASED SKIN TREATMENT DEVICE AVOIDING LIOB IN AIR

(71) Applicant: KONINKLIJKE PHILIPS N.V., Eindhoven (NL)

(72) Inventors: Mark Thomas Johnson, Eindhoven (NL); Petrus Theodorus Jutte, Eindhoven (NL); Bastiaan Wilhelmus Maria Moeskops, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1500 days.

(21) Appl. No.: 14/387,858

(22) PCT Filed: Mar. 26, 2013

(86) PCT No.: PCT/IB2013/052396
§ 371 (c)(1),
(2) Date: Sep. 25, 2014

(87) PCT Pub. No.: WO2013/150415
PCT Pub. Date: Oct. 10, 2013

(65) Prior Publication Data
US 2015/0051593 A1 Feb. 19, 2015

Related U.S. Application Data

(60) Provisional application No. 61/618,880, filed on Apr. 2, 2012.

(51) Int. Cl.
*A61B 18/20* (2006.01)
*A61N 5/06* (2006.01)
(Continued)

(52) U.S. Cl.
CPC .......... *A61B 18/203* (2013.01); *A61N 5/0616* (2013.01); *A61N 5/0617* (2013.01);
(Continued)

(58) Field of Classification Search
CPC ........... A61B 2018/00452; A61B 2018/00476; A61B 2018/00601; A61B 2018/2035; A61B 18/203
(Continued)

(56) References Cited

U.S. PATENT DOCUMENTS 5,586,981 A * 12/1996 Hu ........................ A61B 18/203
606/9
6,995,336 B2 * 2/2006 Hunt ....................... B23K 26/06
219/121.35
(Continued)

FOREIGN PATENT DOCUMENTS

WO 2004068553 A2 8/2004
WO 2005011510 A1 2/2005
(Continued)

OTHER PUBLICATIONS

The Physics of Diffraction Gratings, Publisher: Thermo RGL; Published in 2002.*

*Primary Examiner* — Gary Jackson
*Assistant Examiner* — Zahed Kabir

(57) ABSTRACT

A light based skin treatment device (10, 20) is provided, comprising a light source (18) for providing an incident light beam (21) for treating a skin (30) by laser induced optical breakdown (LIOB) of hair or skin tissue, a transparent exit window (14) for allowing the incident light beam (21) to exit the device (10, 20), and an optical system for focusing the incident light beam (21) into a focal spot (221, 222) in the hair or skin tissue outside the skin treatment device (10, 20). The exit window (14) comprises an outer surface (41, 42, 43, (Continued)

44) having optical scattering properties such that, for a predetermined power and pulse duration of the incident light beam (21), when the outer surface (41, 42, 43, 44) is in contact with a medium having a refractive index equal to a refractive index (n1) of the exit window (14), a dimension of the focal spot is sufficiently small for a power density of the incident light beam (21) in the focal spot to exceed a threshold value for inducing a LIOB phenomenon in the focal spot, and when the outer surface (41, 42, 43, 44) is in contact with a medium having a refractive index equal to a refractive index (n2) of air, a dimension of the focal spot is sufficiently large for a power density of the incident light beam (21) in the focal spot not to exceed the threshold value for inducing a LIOB phenomenon in the focal spot.

11 Claims, 6 Drawing Sheets

(51) Int. Cl.
  *A61B 18/00* (2006.01)
  *A61B 17/00* (2006.01)
(52) U.S. Cl.
  CPC ............. *A61B 2017/00747* (2013.01); *A61B 2017/00761* (2013.01); *A61B 2018/0047* (2013.01); *A61B 2018/00452* (2013.01); *A61B 2018/00476* (2013.01); *A61B 2018/00601* (2013.01); *A61B 2018/20355* (2017.05)

(58) Field of Classification Search
  USPC .............................................. 606/9
  See application file for complete search history.

(56) References Cited

U.S. PATENT DOCUMENTS

| | | | |
|---|---|---|---|
| 7,582,082 B2 * | 9/2009 | Van Hal | A61B 18/203 |
| | | | 606/10 |
| 7,728,295 B2 | 6/2010 | Miles | |
| 2006/0241495 A1 | 10/2006 | Kurtz | |
| 2009/0204109 A1 * | 8/2009 | Grove | A61B 18/203 |
| | | | 606/9 |
| 2010/0004641 A1 | 1/2010 | Frey | |
| 2010/0063490 A1 * | 3/2010 | Verhagen | A61B 5/1077 |
| | | | 606/9 |
| 2010/0069897 A1 * | 3/2010 | Spikker | H01S 3/101 |
| | | | 606/9 |
| 2011/0224660 A1 | 9/2011 | Neuberger | |
| 2012/0123444 A1 * | 5/2012 | Verhagen | A61B 18/20 |
| | | | 606/133 |
| 2015/0238258 A1 * | 8/2015 | Palero | A61N 7/00 |
| | | | 606/9 |

FOREIGN PATENT DOCUMENTS

| | | | |
|---|---|---|---|
| WO | 2007024548 A1 | 3/2007 | |
| WO | 2008001284 A2 | 1/2008 | |

* cited by examiner

LIGHT BASED SKIN TREATMENT DEVICE AVOIDING LIOB IN AIR

This application is the U.S. National Phase application under 35 U.S.C. § 371 of International Application No. PCT/IB2013/052396, filed on Mar. 26, 2013, which claims the benefit of U.S. Provisional Application No. 61/618,880 filed on Apr. 2, 2012. These applications are hereby incorporated by reference herein.

FIELD OF THE INVENTION

This invention relates to a light based skin treatment device comprising a light source, an optical system and a transparent exit window. The light source serves to provide an incident light beam for treating a skin by laser induced optical breakdown (LIOB) of hair or skin tissue. The transparent exit window allows the incident light beam to exit the device. The optical system is provided for focusing the incident light beam into a focal spot in the hair or skin tissue outside the skin treatment device.

BACKGROUND OF THE INVENTION

Such light based skin treatment devices are, e.g., used for wrinkle treatment and for hair cutting. In light based wrinkle treatment, the device creates a focal spot in a dermis layer of the skin to be treated. The power and pulse duration of the laser and the dimension of the focal spot are selected such that a laser induced optical breakdown (LIOB) phenomenon affects the skin in order to stimulate re-growth of skin tissue and, therewith, to reduce wrinkles. In light based hair cutting, the incident light beam is focused inside the hair and the LIOB phenomenon causes the hair to be cut through.

For example, the international patent application published as WO 2005/011510 describes such a device for shortening hairs comprising a laser source for generating a laser beam during a predetermined pulse time, an optical system for focusing the laser beam into a focal spot and a laser beam manipulator for positioning the focal spot in a target position. A dimension of the focal spot and a power of the generated laser beam are such that in the focal spot the laser beam has a power density which is above a characteristic threshold value for hair tissue above which, for the predetermine pulse time, a laser induced optical breakdown (LIOB) phenomenon occurs in the hair tissue.

In general, laser induced optical breakdown (LIOB) occurs in media, which are transparent or semi-transparent for the wavelength of the laser beam, when the power density (W/cm$^2$) of the laser beam in the focal spot exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon.

From experiments it appeared that the LIOB phenomenon can be used to break and shorten hairs growing from skin. Hair tissue is transparent or semi-transparent for wavelengths between approximately 500 nm and 2000 nm. For each value of the wavelength within this range, LIOB phenomena occur in the hair tissue at the location of the focal spot when the power density (W/cm$^2$) of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density decreases when the pulse time increases. It appeared that, in order to achieve mechanical effects as a result of the LIOB phenomenon which are sufficiently effective so as to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ W/cm$^2$. For the described pulse time and with a sufficiently small dimension of the focal spot obtained, for example, by means of a lens having a sufficiently large numerical aperture, this threshold value can be achieved with a total pulse energy of only a few tenths of an mJ.

Whilst it is possible using the device of WO 2005/011510 to generate laser induced optical breakdown (LIOB) with an incident laser beam exiting the device through a small glass "blade" and with sufficient energy to cut human hairs, the products of the LIOB (shock wave, plasma, high power density) can cause destructive damage of the blade. A damaged blade has a detrimental effect on the ability of the device to provide a sufficiently tight focus at the desired position, which may reduce the efficacy of the hair-cutting process and/or may increase the occurrence of adverse side effects, such as skin irritation. Similar problems with LIOB caused damages to the exit window may occur in light based wrinkle devices for wrinkle treatment.

OBJECT OF THE INVENTION

It is therefore an object of the invention to provide a light based skin treatment device as described in the opening paragraph, in which the damage to the exit window is significantly reduced.

SUMMARY OF THE INVENTION

According to a first aspect of the invention, this object is achieved by providing a light based skin treatment device comprising a light source, an optical system and a transparent exit window. The light source serves to provide an incident light beam for treating a skin by laser induced optical breakdown (LIOB) of hair or skin tissue. The transparent exit window allows the incident light beam to exit the device. The optical system is provided for focusing the incident light beam into a focal spot in the hair or skin tissue outside the skin treatment device The exit window comprises an outer surface having optical scattering properties such that, for a predetermined power (W) and pulse duration of the incident light beam, when the outer surface is in contact with a medium having a refractive index equal to a refractive index of the exit window, a dimension of the focal spot is sufficiently small for a power density (W/cm$^2$) of the incident light beam in the focal spot to exceed a threshold value (W/cm$^2$) for inducing a LIOB phenomenon in the focal spot, and when the outer surface is in contact with a medium having a refractive index equal to a refractive index of air, a dimension of the focal spot is sufficiently large for a power density (W/cm$^2$) of the incident light beam in the focal spot not to exceed the threshold value (W/cm$^2$) for inducing a LIOB phenomenon in the focal spot.

Ideally, the LIOB is always generated in the hair or skin tissue. However, in real operation not all hairs or skin tissue are correctly hit and LIOB is generated either in the applied immersion fluid, e.g. water, or in air, if e.g. an air bubble is present. In an extensive series of measurements the inventors have established that the damage to the exit window is far more severe when the LIOB is generated in air than when the LIOB is generated in the immersion fluid or in the target position in the hair or skin. The side effects of the laser induced optical breakdown of gas molecules in air, such as shock wave, plasma and high power density of the light in the focal spot, have appeared to be much more harmful to the exit window than for LIOB in immersion fluids, hair or skin tissue.

With the light based skin treatment device according to the invention, the occurrence of LIOB in air is significantly reduced or even completely avoided by ensuring that the maximum power density (W/cm$^2$) in the focal spot in air remains below the threshold value that has to be reached in order to create LIOB. Two features of the above described light based skin treatment device are important for keeping the maximum power density in the focal spot in air below the LIOB threshold, while still creating LIOB events in the hair or skin tissue.

The first important feature of the light based skin treatment device according to the invention is that the light source and the optical system are arranged to provide the incident light beam with a power (W) and a pulse duration resulting in a maximum power density (W/cm$^2$) in the focal spot which is sufficient for causing LIOB when the outer surface of the exit window is in contact with a medium having a refractive index equal to or close to the refractive index of the exit window. As a result, LIOB will occur in hair or skin tissue.

The second important feature of the light based skin treatment device according to the invention is that the optical scattering properties of the outer surface of the exit window cause the light exiting the skin treatment device to be deflected in several directions if the refractive indices of the exit window and the medium in contact with the outer surface of the exit window substantially differ. The desired optical scattering properties may, e.g., be provided by a structured or deformed outer surface. In principle, a deformed surface and a structured surface are different words for almost the same, i.e. deviations from a completely smooth surface in order to scatter the light beam resulting in an increased dimension of the focal spot. The main difference between a deformed and a structured surface resides in the size of the deviations. For a deformed surface, the deviations have a size in the order of the width of the light beam at the outer surface of the exit window. From a structured surface, the deviations are at a micron level, which is more in the order of the wavelength of the incident light beam. In the following, the term structured surface will be used, without any intention to limit the invention such that larger deformations or other ways for obtaining the desired optical scattering properties of the outer surface would not be possible.

The exit window is typically made of transparent glass or plastics having typical refractive indices between 1.3 and 1.7, more often close to 1.5. With a value of 1.0, the refractive index of air is substantially different. The deflection of the incident light beam at the transition of the exit window and air results in a relatively large focal spot. As a result, LIOB in air and its damaging side effects on the exit window are avoided.

When the structured outer surface of the exit window is in contact with an immersion fluid having a refractive index equal or similar to the refractive index of the exit window, the incident light beam will not, or not significantly, be deflected at the structured outer surface. The refractive index of water is 1.33, which is already much closer to the refractive index of the exit window than the refractive index of 1.0 of air. Preferably, an immersion fluid is used with a refractive index that is even closer to the refractive index of the material of which the exit window is made. When the incident light beam is not deflected at the structured outer surface, the focal spot of the incident light beam will be much smaller and the maximum power density (W/cm$^2$) in the focal spot will be much higher. Also when the outer surface of the exit window is in contact with a hair (refractive index 1.54) or skin tissue (refractive index 1.4), the focal spot will be relatively small and the maximum power density in the focal spot will be relatively high.

It is to be noted that with the word 'air', reference is made to any gas, mixture of gases or vapor that may be present at the skin surface. The main idea behind the invention is to make sure that LIOB will only occur in a medium with a refractive index equal to or similar to that of the exit window. The exact geometry of the structured outer surface, the characteristics of the optical focusing system, and the power and pulse duration of the incident light beam determine how well the refractive indices of the exit window and the medium in contact with the outer surface of the exit window have to match in order to create LIOB. The device may be arranged such that LIOB will only take place in hair or skin tissue and an immersion fluid with the correct refractive index, but not in water or air. Alternatively, the device may be arranged such that LIOB will also occur in water, but still not in air.

In an embodiment of the skin treatment device according to the invention, the outer surface of the exit window has a surface roughness with an RMS value defined by the relation $$(n1-n2)*RMS>C*\lambda,$$

wherein (n1−n2) is a difference between the refractive index (n1) of the exit window and the refractive index (n2) of air, C is a constant with a value between 0.07 and 10, and λ is a wavelength of the incident light beam. Experiments have shown that, independent of the exact structure of the surface irregularities present on the outer surface, such RMS values provide for sufficient reduction of the tightness of the focal spot in order to avoid LIOB in air. In preferred embodiments, C has a value between 0.1 and 5, even more preferably between 0.2 and 3.

The exact value of C to be selected depends on the increase of the power density in the focal spot that is desired when comparing the larger focal spot in air with the smaller focal spot in a hair or other medium with a refractive index close to the refractive index of the exit window. For example, a 100-times increase of the power density in the focal spot requires a value for C of about 1.5.

The light based skin treatment device according to the invention may be a device for optically cutting hair, i.e. a laser shaver, or an optical skin-rejuvenation device, e.g. for reducing skin wrinkles. When the light based skin treatment device is a laser shaver, the exit window may be embodied as an optical blade which, during proper use, emits the incident light beam in a direction parallel to the skin surface. When the light based skin treatment device is an optical skin-rejuvenation device, the incident light beam typically exits the device in a direction perpendicular to the exit window and the skin surface.

In an embodiment of the light based skin treatment device according to the invention, the structured outer surface of the exit window comprises a periodic structure. The periodic structure may have a pitch in the order of a few times, e.g. between 1 and 6 times a wavelength of the incident light beam. Such a periodic structure may form a diffraction grating, which will in addition to defocusing the incident light beam also redistribute some of the beam energy in totally different directions. Of course, this defocusing and energy redistributing effects will only occur in air and other mediums having a refractive index substantially different from the refractive index of the exit window. In such mediums, the maximum power density in the focal spot will be low enough to avoid LIOB.

Alternatively, the structured outer surface of the exit window comprises sand-blasted pits. Although such a structure of the outer surface of the exit window does not show the periodicity of the previously described embodiments, it will also have a sufficiently deteriorating effect on the incident light beam to avoid LIOB in air.

These and other aspects of the invention are apparent from and will be elucidated with reference to the embodiments described hereinafter.

DETAILED DESCRIPTION OF THE INVENTION

Figure 1:
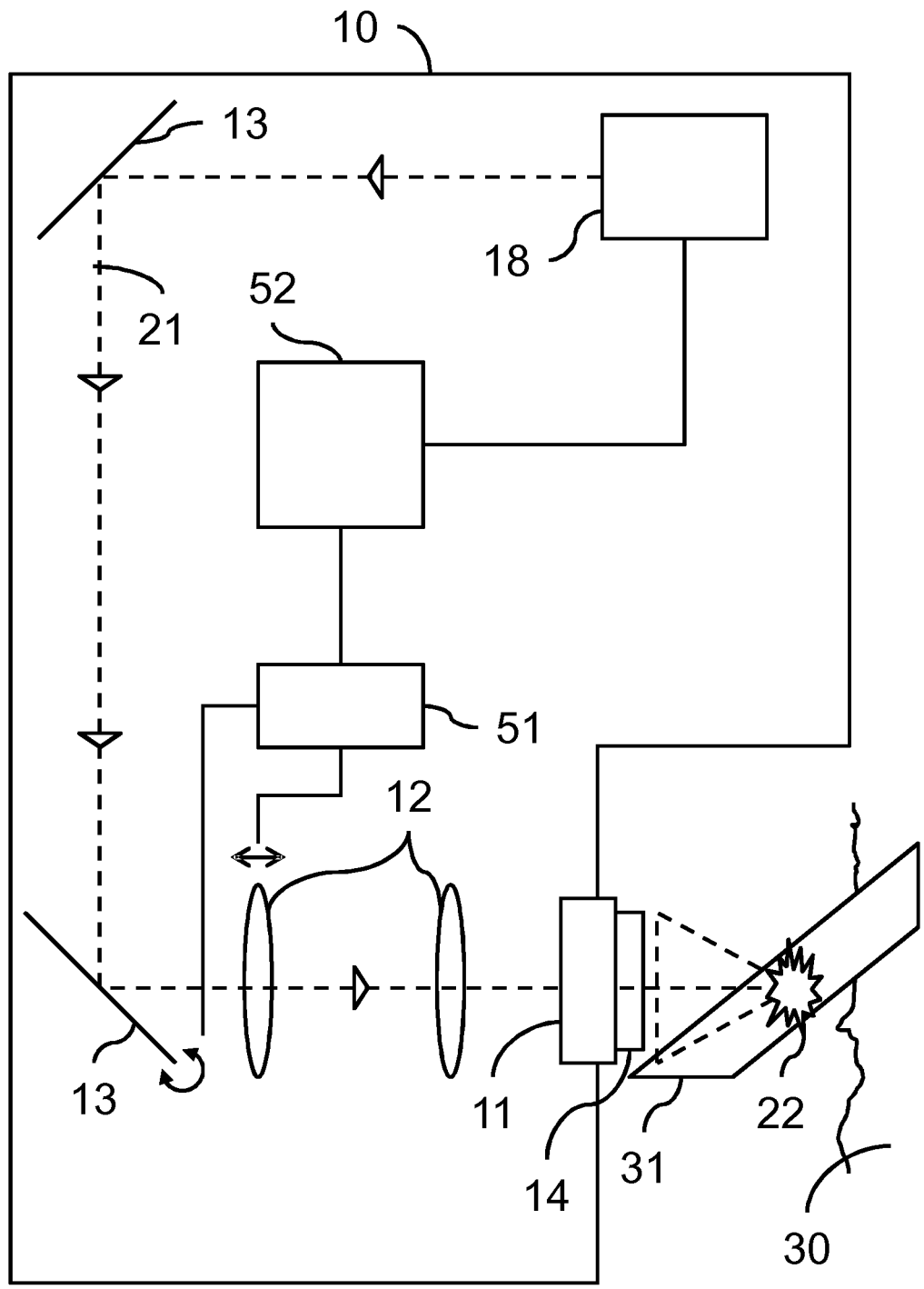
FIG. 1 schematically shows an optical shaver according to the invention.

FIG. 1 schematically shows an optical shaver 10 according to the invention. The optical shaver comprises a light source 18 for providing an incident light beam 21 for cutting hairs 31 growing at human or animal skin 30. The incident light beam 21 is typically a pulsed laser. For example, Nd:YAG lasers with emission at 1064 nm or Er:YAG lasers with emission at 1645 nm are used for laser induced optical breakdown (LIOB) cutting of the hairs 31. Optical elements, such as lenses 12 and mirrors 13, are provided and form an optical system for focusing the pulsed laser beam 21 into a focal spot 22 in the hair 31. The optical elements 12, 13 may be adjustable by a focusing device 51 for adapting the exact position of the focal spot 22 when needed. For this purpose, e.g., the lenses 12 may be translated and/or the mirrors 13 may be rotated. A processor 52 is provided and coupled to, e.g., the light source 18 and the focusing device 51 for controlling their operation.

During use, a skin interface element 11, which may comprise further focusing elements, is moved over the skin 30 surface to be shaved. The skin interface comprises an exit window 14 for allowing the incident light beam 21 to leave the device 10. The exit window 14 is typically embodied as an optical blade for enabling the incident light beam 21 to leave the device in a direction substantially parallel to the skin surface. The exit window 14 is made of a transparent material, such as plastics or glass. Both glass and plastics have a refractive index of about 1.5, which may vary slightly depending on its exact composition. Alternatively, sapphire with a refractive index of about 1.77 is used for the exit window.

Figure 2:
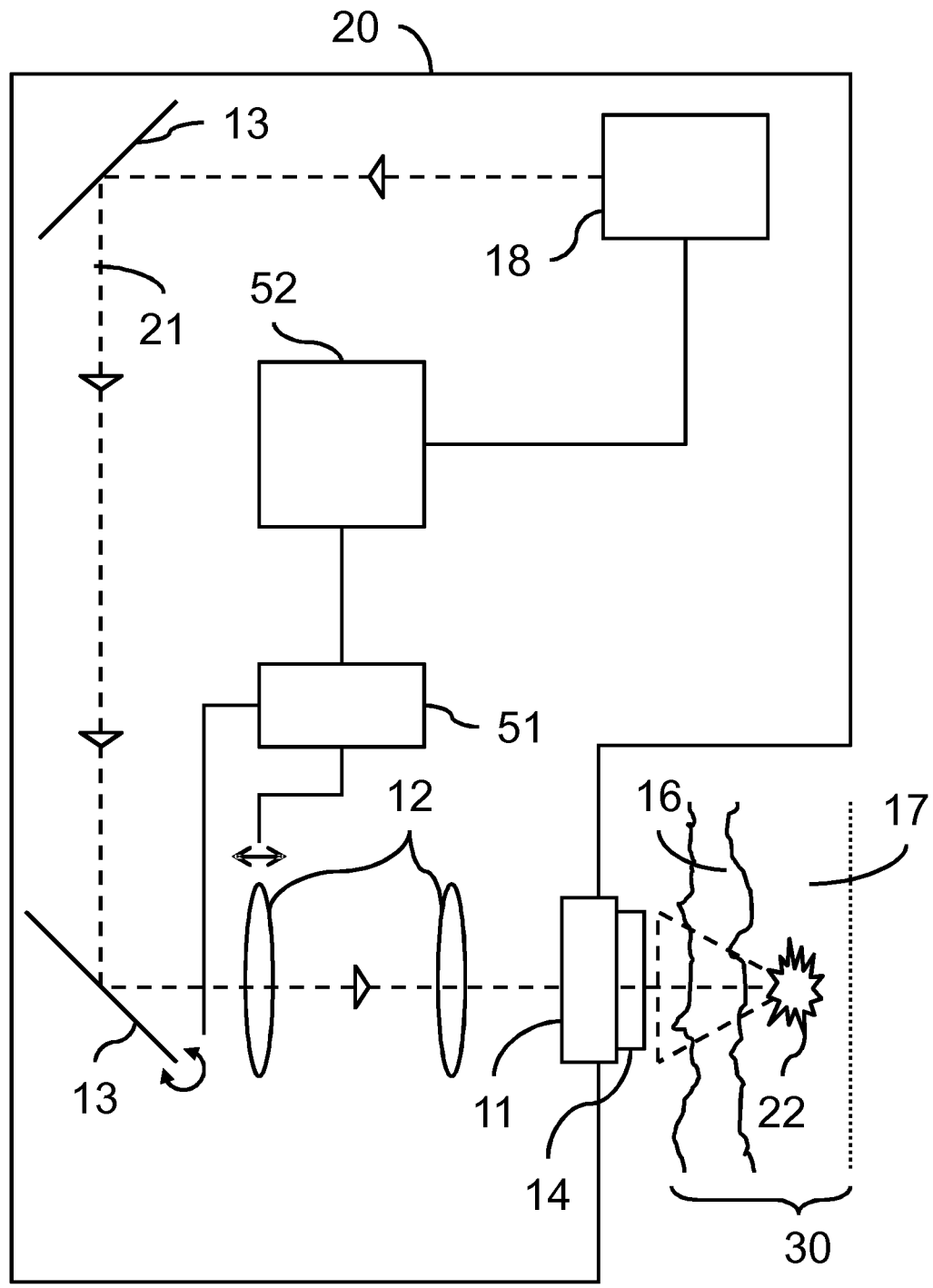
FIG. 2 schematically shows a skin rejuvenation device according to the invention.

FIG. 2 schematically shows a skin rejuvenation device 20 according to the invention. Many of the elements of the skin rejuvenation device 20 are similar to the elements already described above when discussing the optical shaver 10 of FIG. 1. The device 20 is typically used for reducing wrinkles that may appear in human skin 30 as a result of normal aging processes. The skin 30 comprises multiple layers with different optical properties. The epidermis 16 is composed of the outermost layers and forms a waterproof protective barrier. Underneath the epidermis 16, the dermis 17 is situated. The dermis 17 comprises the collagen fibers at which the skin treatment is aimed. The purpose of the skin treatment is to create a focus 22 of the pulsed laser beam 21 in the collagen of the dermis 17 in order to create microscopic lesions which result in new collagen formation and reduced wrinkles.

During use, the skin interface element of the device 20, is pressed onto or kept close to the skin 30 to be treated. The skin interface element 11 of the rejuvenation device 20 does not have an optical blade as used in the optical shaver 10 of FIG. 1. During use, the exit window 14 is held parallel to the skin 30 and the incident light beam 21 leaves the exit window and enters the skin 30 in a direction substantially perpendicular to the skin surface.

In both the optical shaver 10 of FIG. 1 and the skin rejuvenation device 20 of FIG. 1, an immersion fluid may be provided in between the skin interface element 11 and the skin surface. Preferably, an immersion fluid is used with a refractive index close to the refractive index of the exit window 14 and the skin 30 or hair 31 where the LIOB is to occur. For this purpose, fluids with a refractive index of about 1.4 to about 1.5 will be very suitable. Also water, although having a somewhat lower refractive index of 1.33, may for some devices and applications be a suitable immersion fluid.

According to the invention, the exit windows 14 of the optical shaver 10 and the skin rejuvenation device 20 of FIGS. 1 and 2 comprise an outer surface with optical scattering properties such that, for a predetermined power and pulse duration of the incident light beam 21, when the outer surface is in contact with a medium having a refractive index equal to a refractive index of the exit window, the focal spot is sufficiently small for a power density of the incident light beam in the focal spot to exceed a LIOB threshold, and when the outer surface is in contact with air, the focal spot is sufficiently large for the power density of the incident light beam not to exceed the LIOB threshold.

The desired scattering properties may, e.g., be provided by a structured or deformed surface. In principle, a deformed surface and a structured surface are different words for almost the same, i.e. deviations from a completely smooth surface in order to scatter the beam and increase the size of the focus. The main difference between deformed and structured is the size of the deviations. For a deformed surface, the deviations have a size in the order of the width of the light beam at the exit window. From a structured surface, the deviations are at a micron level, which is more in the order of the wavelength of the incident light beam. In the following, the term structured surface will be used, without any intention to limit the invention such that larger deformations or other ways for obtaining the desired scattering properties are not possible. The structured surface should at least cover those surface areas of the exit window 14 where the incident light beam 21 may leave the device 10, 20. Preferably, the structured surface covers the whole surface area of the exit window 14.

Figure 3A:
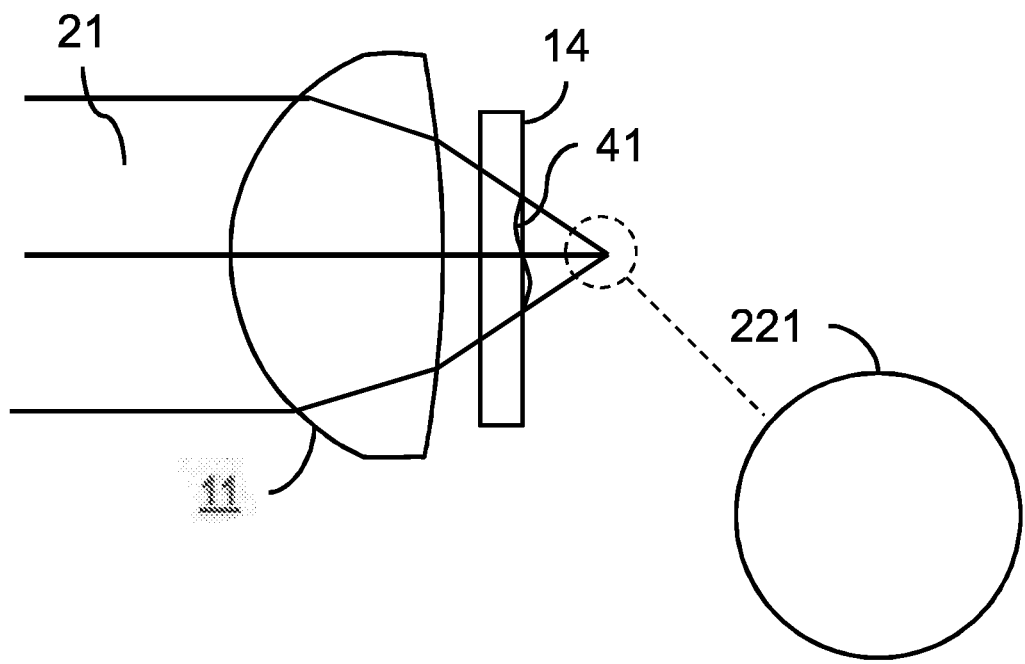
FIGS. 3a and 3b illustrate the effect of using an exit window with a structured surface.
Figure 3B:
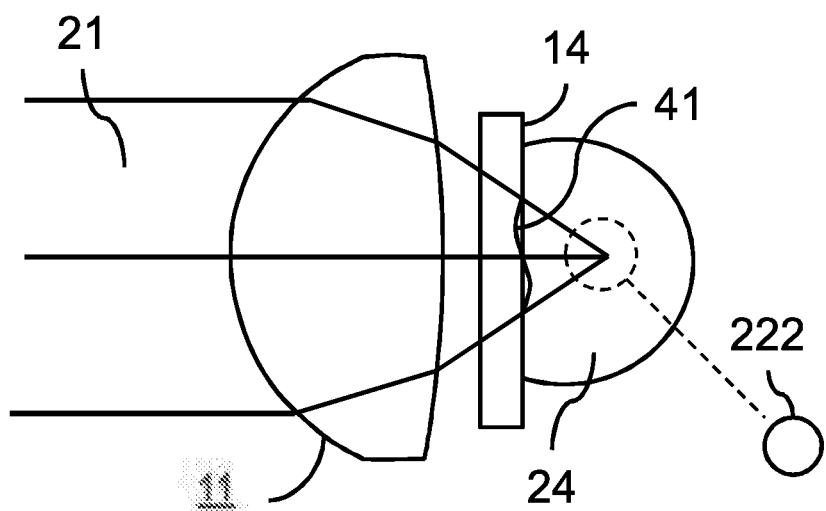

FIGS. 3a and 3b illustrate the effect of using an exit window 14 with a structured surface 41. In both figures the incident light beam 21 is focused by a focusing element 11 and leaves the device 10, 20 through the exit window 14 to form a focus in the focal spot 221, 222. At the position of the exit window 14 where the incident light beam 21 leaves the device 10, 20, the exit window 14 has a structured surface 41. In FIG. 3a, the exit window 14 borders on air. In FIG. 3b, the exit window 14 borders on an immersion fluid 24 with a refractive index similar to the refractive index of the index window 14. Because of the structured surface 41 and the different, i.e. lower, refractive index of air, the incident light beam 21 of FIG. 3a is deteriorated, resulting in a larger focal spot 221 and lower maximum light intensities in the focal spot 221. According to the invention, the power of the incident light beam 21 is such that the power density in this larger spot 221 will not be sufficient to create LIOB. In FIG. 3b, because of the substantially matching refracting indices of the exit window 14 and the immersion fluid 24, the structured surface 41 does not have a deteriorating effect on the incident light beam and a tight focal spot 222 is created with substantially higher maximum light intensities in this focal spot 222. According to the invention, the power of the incident light beam 21 is such that the power density in this smaller spot 221 will be above the LIOB threshold. Thus, LIOB will only be created inside the immersion fluid and in hair and skin tissue, which also have a refractive index close to that of the exit window. No LIOB in air will be created and damage the exit window 14 surface. If, e.g., air bubbles will be formed in the immersion fluid 24 at the surface of the exit window 14, the structured surface 41 will cause deterioration of the incident light beam and LIOB in air will be avoided.

Figure 4A:
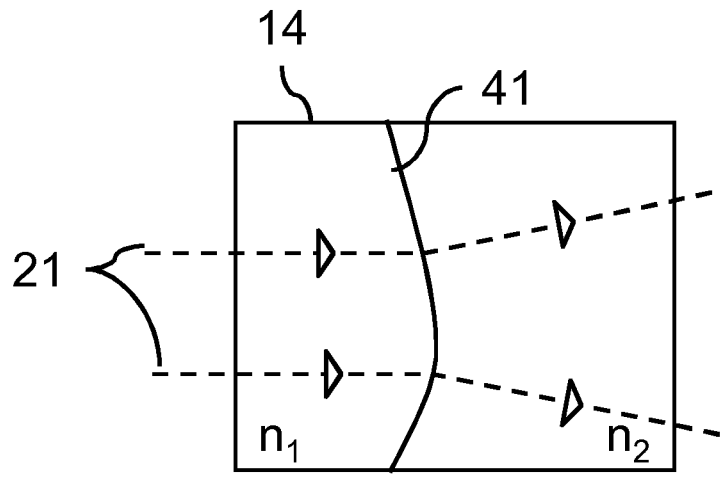
FIGS. 4a and 4b illustrate the physical principle behind the use of the structured surface.
Figure 4B:
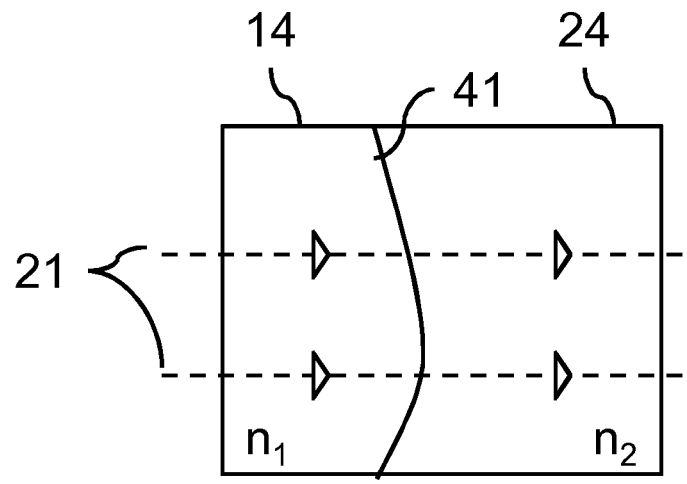

FIGS. 4a and 4b illustrate the physical principle behind the use of the structured surface 41. In FIG. 4a, the exit window 14 is in contact with air, which has a different refractive index than the material of the exit window 14. In FIG. 4b, the exit window 14 is in contact with an immersion fluid 24, which has a refractive index that is substantially equal to the refractive index of the material of the exit window 14. The structured surface 41 is not smooth, like in the prior art, but encloses different angles with the incident light beam 21 at different positions.

In the situation of FIG. 4a, the incident light beam 21 will, because of the difference in refractive index, be deflected at the interface between the exit window 14 material and the air. Because the deflection will be different at different positions at the structured surface 41, it will also be different for different parts of the incident light beam 21. As a result, the light beam 21 will be deteriorated and the focal spot 221 will be larger (see FIG. 3a) than when the exit window 14 would have had a flat surface.

In FIG. 4b, the incident light beam 21 will not experience a change in refractive index at the interface between the exit window 14 and the immersion fluid. No deflection of light will occur and the size of the focal spot 222 (see FIG. 3b) will not be affected by the varying surface orientations of the structured surface 41. Experiments have shown that going from a focal spot with a 100 microns diameter to a 3 microns diameter may result in an increase of peak optimal power from about 0.1 GWmm$^{-2}$ to about 14 GWmm$^{-2}$, which is more than enough to move from below the LIOB threshold to above the LIOB threshold.

Figure 5A:
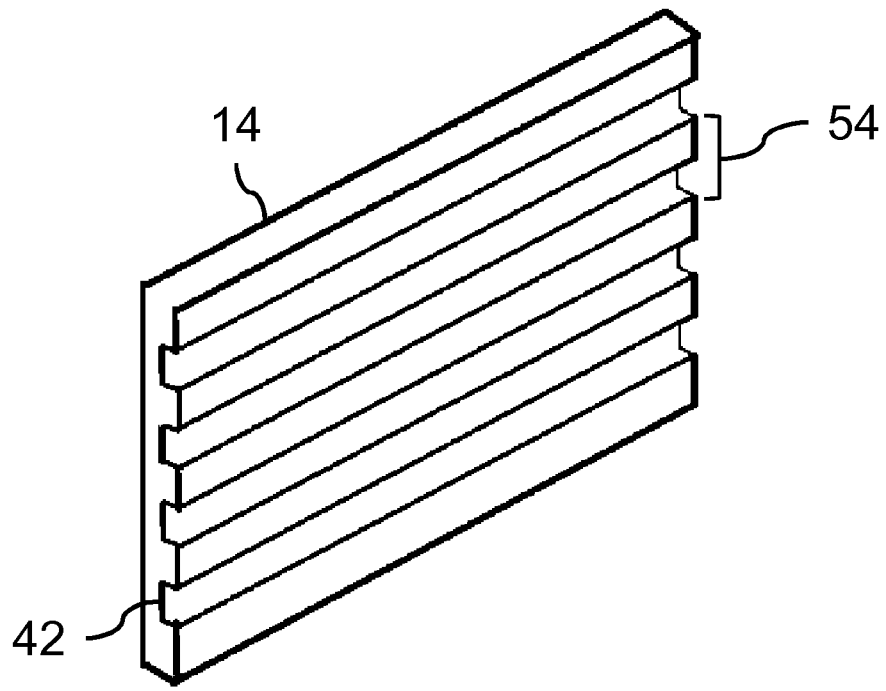
FIGS. 5a, 5b and 6 show exemplary embodiments of exit windows with structured surfaces.
Figure 5B:
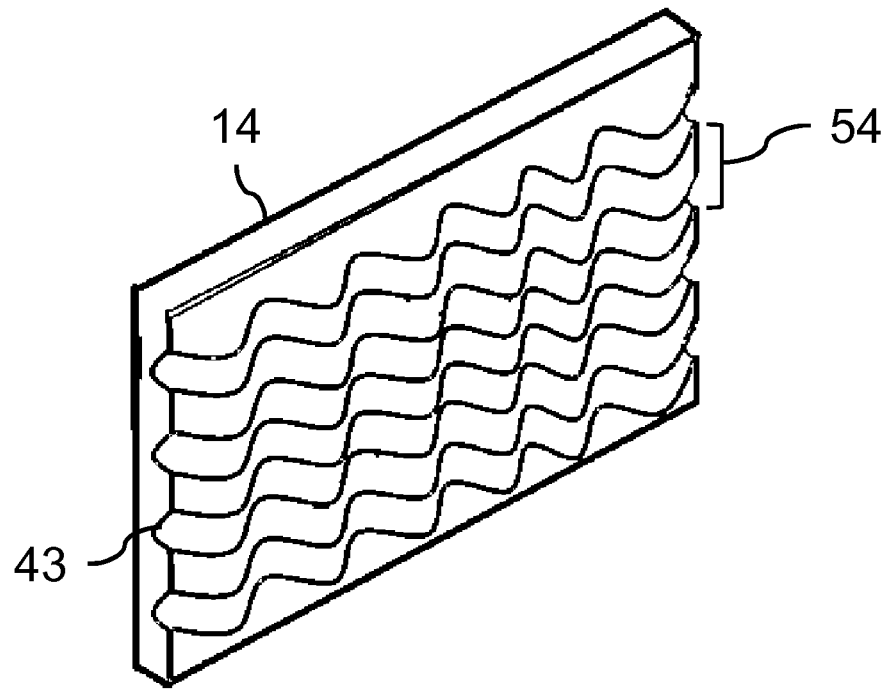
Figure 6:
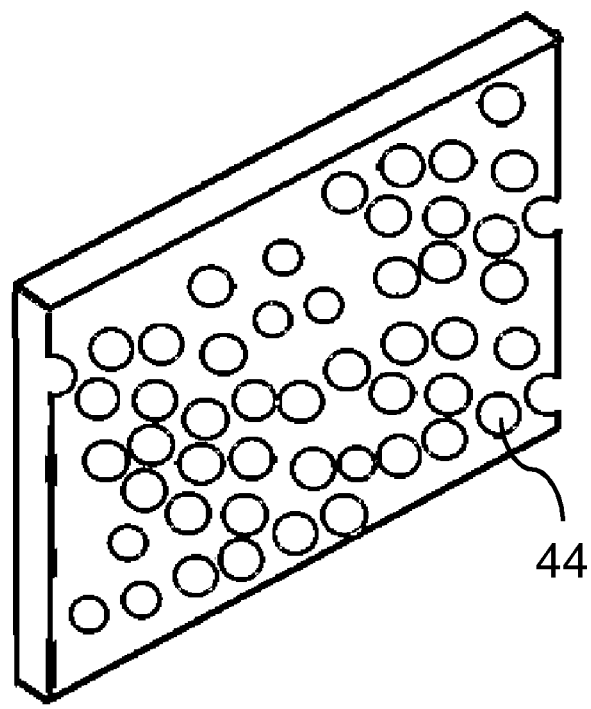

FIGS. 5a, 5b and 6 show exemplary embodiments of exit windows 14 with structured surfaces. In FIGS. 5a and 5b, the structures surfaces have a periodic pattern 42, 43 with a constant pitch 54. The pitch 54 is the distance between two consecutive variations in the surface structure. For an optimal light beam 21 deteriorating effect, the pitch 54 should not be larger than a few times the wavelength of the incident light beam 21. A further aspect of the pattern that influences the light deteriorating effect is the surface roughness of the exit window which may be defined as a depth of the grooves in FIGS. 5a and 5b. For a 1645 nm laser, groove depths between 0.2 and 30 microns are suitable for obtaining the desired effect. Grooves with a depth between around 0.5 and 10 microns are preferred for even better results. The groove depth may be varied stepwise or gradually. For laser light with larger wavelengths, the groove depth should be increased proportionally to obtain a similar effect on the size of the focal spot. Surface roughness may be defined by an RMS value. The RMS value of a surface is the root mean squared of the height or depth of all surface irregularities. For a regularly structured surface with equally shaped grooves, the RMS value equals the groove depth.

In general, the relation between a minimal RMS value, refractive index and wavelength of the incident light can be represented by the following relation:

$$(n_1-n_2)*RMS > C*\text{wavelength},$$

wherein $(n_1-n_2)$ is the difference in refractive index between the exit window material and the adjacent medium (e.g. 0.5 for glass and air or 0.2 for glass and water, 0.7 for sapphire and air). C is a constant with preferred values between 0.07 and 10, more preferably between 0.1 and 5 and most preferably between 0.2 and 3.

The exact value of C to be selected depends on the increase of the power density in the focal spot that is desired when comparing the larger focal spot in air to the smaller focal spot in a hair or other medium with a refractive index close to the refractive index of the exit window material. For example, a 100-times increase of the power density in the focal spot requires a value for C of about 1.5.

In FIG. 5a, the surface structure comprises a stepped pattern 42. In FIG. 5b, the surface structure comprises a regular wavy pattern 43. Many variations on such regular patterns 42, 43, such as saw tooth patterns or checkerboard patterns, can be used. Such regular patterns 42, 43 may cause the surface structure to function as a diffraction grating, which does not only enlarge the focal spot size but also effects the power density distribution in the focal spot.

FIG. 6 shows an irregular pattern that may, e.g., be obtained by sandblasting methods or other random processes for providing or altering the surface structure. Both the size and the position of the pits 44 may be distributed irregularly. For an optimal light beam deteriorating effect, the pits 44 in such a pattern do preferably not have a size larger than a few times the wavelength of the incident light beam 21.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A light based skin treatment device comprising:
a light source for providing a pulsed incident light beam having a predetermined power and pulse duration for treating a skin by laser induced optical breakdown (LIOB) of hair or skin tissue,
a transparent exit window for allowing the incident light beam to exit the device, and
an optical system for focusing the incident light beam into a focal spot in the hair or skin tissue outside the skin treatment device, wherein
the exit window comprises an outer surface having optical scattering properties such that, for the predetermined power and pulse duration of the incident light beam,
when the outer surface is in contact with a medium having a refractive index equal to a refractive index of the exit window, a dimension of the focal spot is sufficiently small for a power density of the incident light beam in the focal spot to exceed a threshold value for inducing a LIOB phenomenon in the focal spot, and
when the outer surface is in contact with a medium having a refractive index equal to a refractive index of air, a dimension of the focal spot is sufficiently large for a power density of the incident light beam in the focal spot not to exceed the threshold value for inducing a LIOB phenomenon in the focal spot.

2. A light based skin treatment device as claimed in claim 1, wherein the outer surface has a surface roughness with an RMS value defined by the relation $$(n1-n2)*RMS>C*\lambda,$$

wherein (n1−n2) is a difference between the refractive index n1 of the exit window and the refractive index n2 of air, C is a constant with a value between 0.07 and 10, and $\lambda$ is a wavelength of the incident light beam.

3. A light based skin treatment device as claimed in claim 2, wherein C has a value between 0.1 and 5.

4. A light based skin treatment device as claimed in claim 1, wherein the outer surface comprises a structured surface.

5. A light based skin treatment device as claimed in claim 4, wherein the structured surface comprises a periodic structure.

6. A light based skin treatment device as claimed in claim 5,
wherein the incident light beam is a pulsed laser; and
wherein the periodic structure has a pitch of between 1 and 6 times a wavelength of the pulsed laser.

7. A light based skin treatment device as claimed in claim 5, wherein the periodic structure forms a diffraction grating.

8. A light based skin treatment device as claimed in claim 4, wherein the structured surface comprises random irregularities.

9. A light based skin treatment device as claimed in claim 8, wherein the random irregularities are sand-blasted pits.

10. A light based skin treatment device as claimed in claim 1, wherein the outer surface comprises a deformed surface.

11. A light based skin treatment device as claimed in claim 1, wherein the treating of the skin comprises optically cutting a hair, and wherein the exit window is part of an optical blade for enabling the incident light beam to exit the device in a direction substantially parallel to a surface of the skin.

* * * * *